US008900433B2

(12) United States Patent
Carpenter et al.

(10) Patent No.: US 8,900,433 B2
(45) Date of Patent: Dec. 2, 2014

(54) LOW-SLOPE PH ELECTRODE

(75) Inventors: Frank Howland Carpenter, Fort Collins, CO (US); John Robert Woodward, Windsor, CO (US); Karl Lewis King, Windson, CO (US)

(73) Assignee: Hach Company, Loveland, CO (US)

(*) Notice: Subject to any disclaimer, the term of this patent is extended or adjusted under 35 U.S.C. 154(b) by 175 days.

(21) Appl. No.: 13/509,412

(22) PCT Filed: Nov. 8, 2010

(86) PCT No.: PCT/US2010/055830
§ 371 (c)(1),
(2), (4) Date: May 11, 2012

(87) PCT Pub. No.: WO2012/067598
PCT Pub. Date: May 24, 2012

(65) Prior Publication Data
US 2012/0241320 A1 Sep. 27, 2012

Related U.S. Application Data

(60) Provisional application No. 61/260,503, filed on Nov. 12, 2009.

(51) Int. Cl.
*G01N 27/333* (2006.01)
*G01N 27/36* (2006.01)
*G01N 27/30* (2006.01)
*G01N 33/18* (2006.01)
*G01N 33/15* (2006.01)
*G01N 33/02* (2006.01)

(52) U.S. Cl.
CPC ............. *G01N 27/36* (2013.01); *G01N 33/18* (2013.01); *G01N 33/15* (2013.01); *G01N 27/302* (2013.01); *G01N 33/02* (2013.01)
USPC ............................... 204/433; 204/416

(58) Field of Classification Search
CPC ... G01N 27/302; G01N 27/333; G01N 27/36; C03C 4/18
See application file for complete search history.

(56) References Cited

U.S. PATENT DOCUMENTS 3,188,285 A * 6/1965 Watanabe et al. ............. 204/415
3,458,422 A * 7/1969 Proctor, Jr. ................... 204/420
(Continued)

FOREIGN PATENT DOCUMENTS

| GB | 126065 | | 1/1972 | |
| GB | 1304117 | * | 1/1973 | ............. G01N 27/36 |
| GB | 1420126 | | 1/1976 | |

OTHER PUBLICATIONS

International Searching Authority, Search Report for International Application PCT/US2010/055830, Apr. 18, 2012, 4 pages (EPO).
(Continued)

Primary Examiner — Alex Noguerola
(74) Attorney, Agent, or Firm — Ference & Associates LLC (57) ABSTRACT

A low-slope pH electrode (100) is provided according to an embodiment of the invention. The low-slope pH electrode (100) includes an electrode body (102), a pH-sensitive glass (122) fused into the electrode body (102), with the pH-sensitive glass (122) including a predetermined area, and a mask (124) formed over a predetermined portion of the predetermined area of the pH-sensitive glass (122) in order to form a low-slope pH characteristic. At least a portion of an ion exchange performed by the pH-sensitive glass (122) is blocked by the mask (124).

21 Claims, 6 Drawing Sheets

(56) References Cited

U.S. PATENT DOCUMENTS

| | | | |
|---|---|---|---|
| 4,218,299 A | | 8/1980 | Lindell et al. |
| 5,016,201 A | * | 5/1991 | Bryan et al. .................. 700/267 |
| 6,740,216 B2 | | 5/2004 | Diakonov et al. |
| 2003/0150726 A1 | | 8/2003 | West et al. |

OTHER PUBLICATIONS

Cheng, K. L., et al., "The Deviation Potential of pH Glass Electrode", Mikrochimica Acta (Wien), 1985, pp. 95-101, vol. 1, Springer-Verlag, New York, New York, USA.

* cited by examiner

LOW-SLOPE PH ELECTRODE

BACKGROUND OF THE INVENTION

1. Field of the Invention

The invention is related to the field of pH electrodes, and in particular, to a low-slope pH electrode.

2. Statement of the Problem

A measure of the ionic concentration of a fluid is desirable in many situations, including testing of fluids in manufacturing settings, for pharmaceutical production, food processing and/or food quality, water quality testing, etc. Measurement of an ionic concentration or activity can indicate completion of a reaction, indicate fractions of components, etc. One measure can comprise a measure of pH, which comprises a measure of acidity of the fluid being tested. The pH measurement can indicate the acidic or basic condition or concentration of the fluid.

A pH measurement comprises a measurement of hydrogen ions in a solution, expressed as a logarithmic number between about zero and fourteen (sometimes extending into negative numbers for exceedingly acidic solutions). On the pH scale, a very acidic solution has a low pH value, such as zero or one, corresponding to a large concentration of hydrogen ions ($H^+$). In contrast, a very basic solution has a high pH value, corresponding to a very small number of hydrogen ions (or to a correspondingly large number of $OH^-$ ions). A neutral solution, such as substantially pure water, has a pH value of about seven.

A pH electrode is an electrode that generates a voltage potential in relation to the pH level of a solution. Sensitivity and accuracy are obviously important characteristics of a pH electrode. Glass electrodes that are used as pH sensors are designed to respond to the pH of a solution, with the measured electrical potential (mV) being plotted on the Y-axis, and pH units being plotted on the X-axis of a graph.

Figure 1:
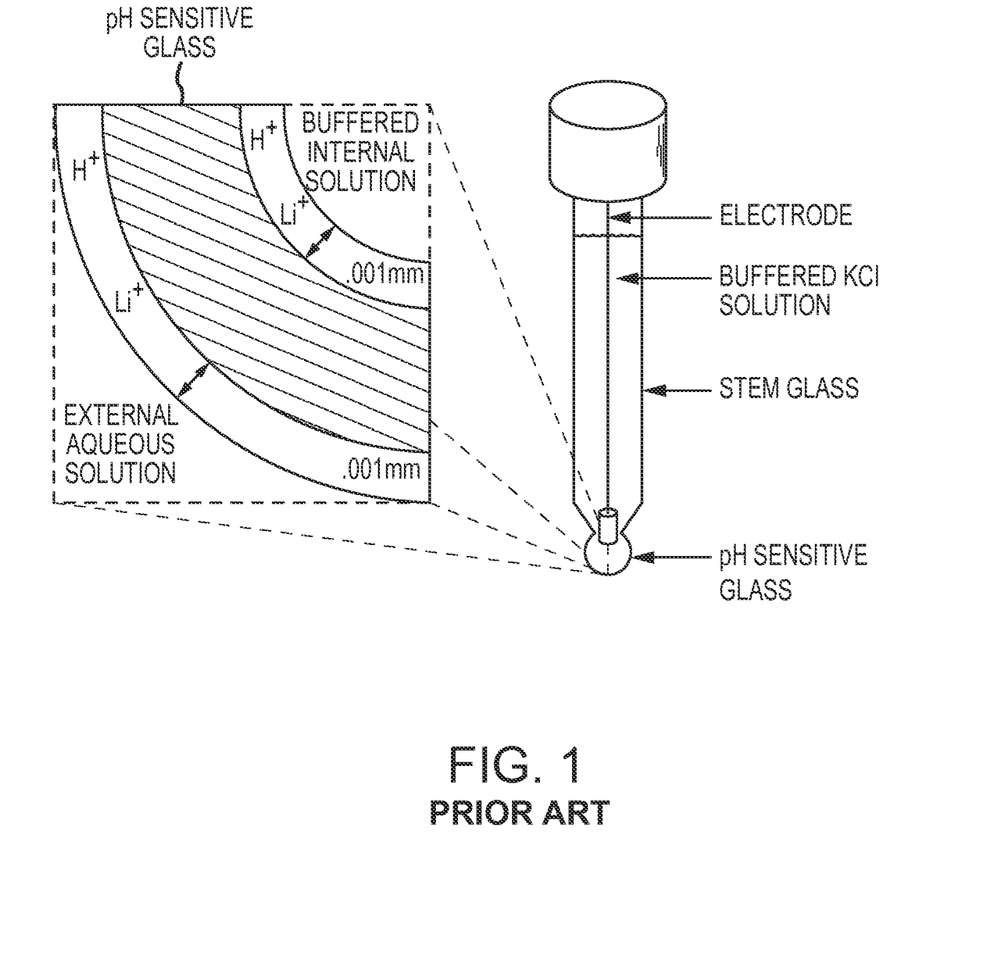
FIG. 1 shows a prior art pH electrode.

FIG. 1 shows a prior art pH electrode. The prior art pH electrode is a glass tube with an ion sensitive glass bulb at one end and the tube further includes an electrolyte and internal electrode element. The prior art pH electrode is typically constructed of two types of glass. The stem of the electrode is a non-conductive, non-responsive glass, while the tip, which is most often bubble-shaped, is a specially formulated pH sensitive lithium ion-conductive glass consisting of the oxides of silica, lithium, and other elements. The structure of the pH glass allows lithium ions to be exchanged with hydrogen ions in aqueous solutions, forming a hydrogen ion responsive layer on the outside of the bulb. A millivolt potential is created across the interface between the pH-sensitive glass and the external aqueous solution. The internal electrolyte interacts with the ion sensitive glass, forming an internal potential.

The magnitude of the potential on the outer surface is dependent on the pH value of the solution being measured. The difference between the external and internal surface voltage potentials ($V_{external}$ minus $V_{internal}$) that are created at the outer and inner hydrated layers of the pH glass can be measured through electro-chemical contact by an internal electrode at least partially immersed in an internal electrolyte solution. Since the internal solution of the glass electrode is held at a constant pH, the measured potential difference is dependent only upon the pH value of the external solution being measured.

A reference electrode is often included in a separate chamber and solution that are also in ionic communication with the fluid being tested. A voltage potential between the two electrodes is thereby formed, similar to a battery. The voltage potential that is developed between the electrodes is directly related to the hydrogen ion concentration of the solution. The reference electrode provides a stable potential against which the measuring electrode can be compared. The voltage potential can be processed according to a table, formula, or other algorithm to arrive at an ionic concentration measurement, such as a pH value, for example.

Aspects of the Invention

In one aspect of the invention, a low-slope pH electrode comprises:
  an electrode body;
  a pH-sensitive glass fused into the electrode body, with the pH-sensitive glass including a predetermined area; and
  a mask formed over a predetermined portion of the predetermined area of the pH-sensitive glass in order to form a low-slope pH characteristic, wherein at least a portion of an ion exchange performed by the pH-sensitive glass is blocked by the mask.

Preferably, the low-slope pH electrode further comprises an electrode element positioned inside the electrode body, a pH buffer solution substantially filling the electrode body, and a seal that substantially seals the electrode body.

Preferably, the mask comprises a non-hydrogen ion responsive material.

Preferably, the mask comprises a non-hydronium ion responsive material.

Preferably, the mask comprises a substantially non-porous material.

Preferably, the mask comprises a minimally porous material.

Preferably, the mask is formed on an external surface of the pH-sensitive glass.

Preferably, the mask is formed of a predetermined thickness.

Preferably, the mask is formed in a predetermined pattern.

Preferably, the mask is formed on one or both of an external surface or an internal surface of the pH-sensitive glass.

Preferably, the low-slope pH electrode comprises a non-Nernstian pH electrode.

In one aspect of the invention, a method of forming a low-slope pH electrode comprises:
  forming an electrode body including a sensor opening;
  fusing a pH-sensitive glass of a predetermined area into the sensor opening; and
  masking a predetermined portion of the predetermined area in order to form a low-slope pH characteristic, wherein at least a portion of an ion exchange performed by the pH-sensitive glass is blocked.

Preferably, the method further comprises positioning an electrode element inside the electrode body, substantially filling the electrode body with a pH buffer solution, and substantially sealing the electrode body.

Preferably, the mask comprises a non-hydrogen ion responsive material.

Preferably, the mask comprises a non-hydronium ion responsive material.

Preferably, the mask comprises a substantially non-porous material.

Preferably, the mask comprises a minimally porous material.

Preferably, the mask is formed on an external surface of the pH-sensitive glass.

Preferably, the mask is formed of a predetermined thickness.

Preferably, the mask is formed in a predetermined pattern.

Preferably, the mask is formed on one or both of an external surface or an internal surface of the pH-sensitive glass.

Preferably, the low-slope pH electrode comprises a non-Nernstian pH electrode.

DESCRIPTION OF THE DRAWINGS

The same reference number represents the same element on all drawings.

DETAILED DESCRIPTION OF THE INVENTION

FIGS. 1-6 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 2:
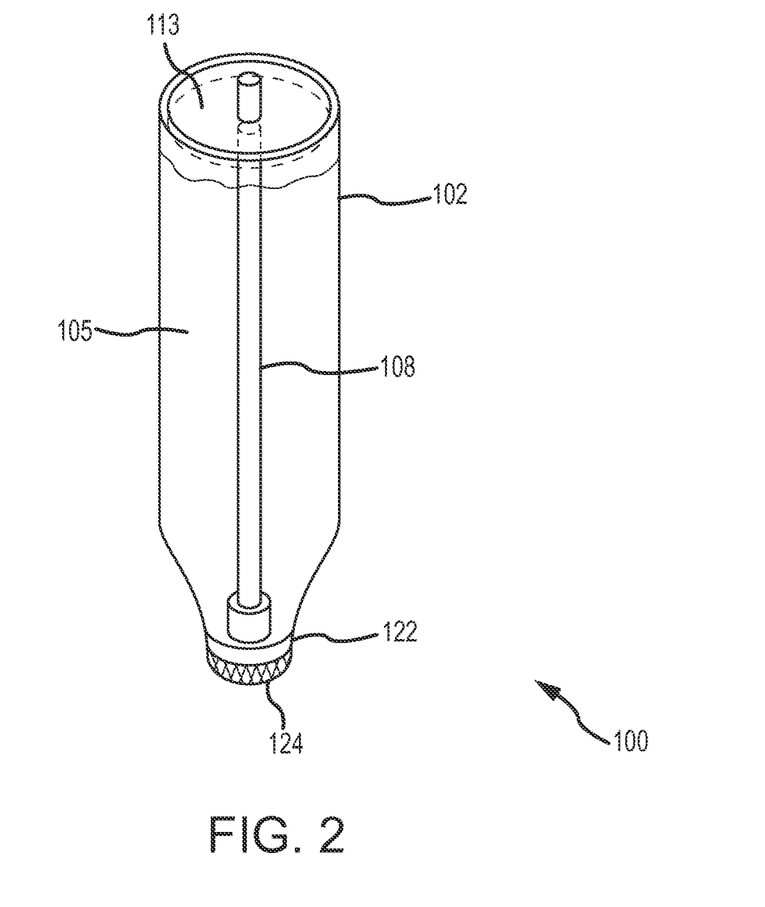
FIG. 2 shows a low-slope pH electrode according to an embodiment of the invention.

FIG. 2 shows a low-slope pH electrode 100 according to an embodiment of the invention. The low-slope pH electrode 100 in the embodiment shown includes an electrode body 102, an electrode element 108, a pH buffer solution 105 substantially filling the electrode body 102, and a region of pH-sensitive glass 122. A seal 113 substantially seals the electrode body 102. The region of pH-sensitive glass 122 in this embodiment is located at a tip or end region of the electrode body 102, but it should be understood that the region of pH-sensitive glass 122 could be located anywhere on the electrode body 102. Further, the low-slope pH electrode can be formed in any desired shape and size. Alternatively, the pH-sensitive glass 122 can comprise any other suitable pH-sensitive material.

The invention creates a low slope pH glass electrode using a standard glass pH electrode and an insulating material applied to an area of the glass. The invention solves the problem of creating a low slope pH electrode by partially covering the surface of a standard glass pH bulb with a non-porous, non-hydronium-ion responding substance.

In use, lithium ions from the glass are exchanged with hydrogen ions in aqueous solutions, forming a responsive layer on the outside of the pH-sensitive glass 122. Consequently, a millivolt potential develops across the interface between the pH-sensitive glass 122 and the external aqueous solution. The internal electrolyte interacts with the pH-sensitive glass 122 and transmits the potential developed by the ions at the outside of the pH-sensitive glass 122 to the internal electrode element 108.

The region of pH-sensitive glass 122 includes a mask 124. The pH-sensitive glass 122 comprises a predetermined area. The mask 124 covers a predetermined portion of that predetermined area.

The size of the predetermined mask portion/area can be varied as desired in order to control the slope of the ionic response of the low-slope pH electrode. If the mask 124 covers a relatively small portion of the area of the pH-sensitive glass 122, the slope may be relatively large (as compared to a pH electrode without a mask). If the mask 124 covers a relatively large portion of the area of the pH-sensitive glass 122, the slope will be relatively low. In some embodiments, the slope may approach zero, wherein ion exchange across the pH-sensitive glass 122 will be minimal (or essentially non-existent).

The mask 124 can comprise any non-hydrogen ion responsive material. The mask 124 can be completely non-porous in some embodiments. The mask 124 can be substantially non-porous or can be minimally porous, so that hydrogen/hydronium ions are kept away from the surface of the pH-sensitive glass 122.

The mask 124 can be formed of any practical thickness. The thickness is important only so long as ions cannot reach the surface of the pH-sensitive glass 122.

The mask 124 can comprise a uniform layer. The mask 124 can be patterned or applied in any desired non-uniform matter. The characteristic of interest is the area of the mask 124 in relation to the area of the pH-sensitive glass 122, wherein the ratio of the area of the mask 124 to the area of the pH glass 122 can be controlled in order to affect the slope of the ion exchange characteristic.

The mask 124 can be melted to or otherwise permanently affixed to the pH-sensitive glass 122. The mask 124 can be bonded or adhered to the pH-sensitive glass 122. The mask 124 can be held to the pH-sensitive glass 122 by static or through tackiness or other semi-adherence. The mask 124 can comprise an adhesive tape or film. The mask 124 can be sprayed on or otherwise deposited on the pH-sensitive glass 122. The mask 124 can be held to the electrode body by any manner of structure.

In some embodiments, the mask 124 is applied to the exterior surface of the pH-sensitive glass 122, as is shown in the figure. The low-slope pH electrode 100 reduces the outer surface area available to the hydronium ions in the solution to be measured.

This is achieved by coating various sections of the outer surface of the pH-sensitive glass 122 with masks 124 including nail polish, Dow DP 190 epoxy resin, or hot-melt adhesive, for example. The use of these compounds to cover varying amounts of glass is only illustrative of the principle. There are numerous other compounds that can be used including but not limited to a non-pH sensitive glass, plastic polymers, epoxy resins, and any other sufficiently non-porous materials.

The mask material in some embodiments may be non-reactive with hydrogen ions. However, it should be understood that any suitable material or materials may be used.

The mask 124 can comprise a single material in some embodiments. Alternatively, the mask 124 can comprise multiple layers, including layers of similar or different materials. The layers can be similar in composition, thickness, or various other material properties, or may differ.

Figure 3:
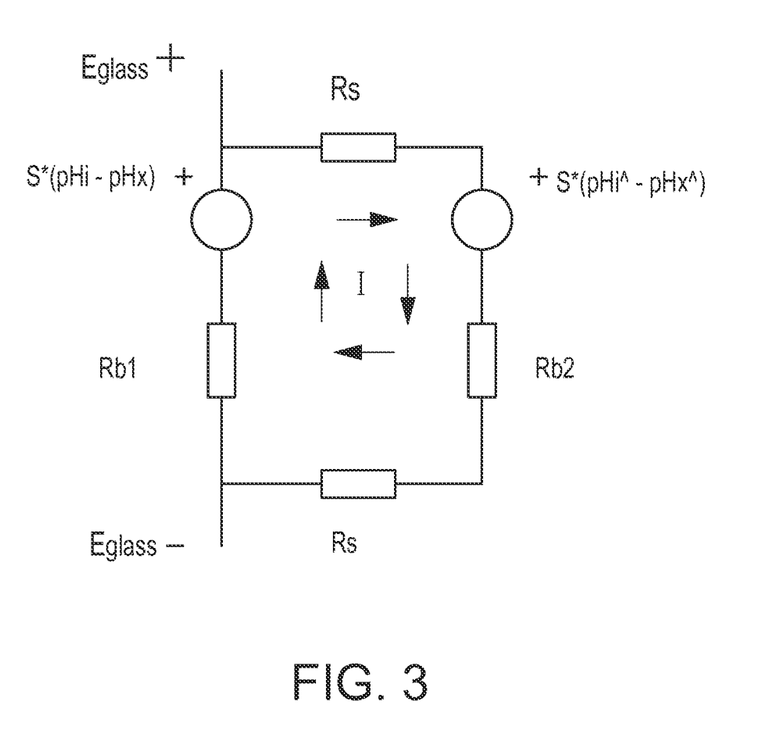
FIG. 3 is a model of a low-slope pH electrode according to the invention.

FIG. 3 is a model of the low-slope pH electrode 100 according to the invention. In the figure, the Eglass term is the electrode potential to be measured and (S) is the slope of the glass' voltage potential ionic response in mV/pH. The (Rs) term is the electrical resistance in the hydrated surface layer and the (Rb) term is the electrical resistance in the bulk glass (i.e., in the glass electrode body 102). The (pHi) term is the pH value (or measurement) at the internal surface of the bulk glass electrode body 102 and the (pHx) term is the pH value at the external surface of the bulk glass electrode body 102.

The (pHi^) term is the pH value (or measurement) at the internal surface of the coated or masked pH-sensitive glass 122 and the (pHx^) term is the pH value at the external surface of the coated or masked pH-sensitive glass 122.

The pH of the internal fill solution is assumed to be 7, but could be a different pH. The total resistance $R_{TOTAL}$ around the loop in the figure can be represented as:

$$R_{TOTAL} = \Sigma R = Rb1 + Rb2 + 2*Rs \quad (1)$$

$$Eglass = (S/\Sigma R)*[(pHi-pHx)*(Rb2+2Rs)+Rb1*(pHi\hat{}-pHx\hat{})] \quad (2)$$

The four cases of interest are:
1) No coating applied, where pHi^=pHi, and pHx^=pHx;
2) External coating applied, where pHi^=pHi, and pHx^=effective internal glass pH;
3) Internal coating applied, where pHi^=effective internal glass pH and pHx^=pHx; and
4) External and internal coating applied, where pHi^=pHx^=effective internal glass pH.

Empirical testing suggests that the effective internal glass pH lies between 7 and 10 for most commercial silicate glass formulations, though other values are possible. Substituting in the various expressions for pHx^ and pHi^, the four cases provide:
1) Eglass=S*(pHi−pHx);
2) Eglass=(S/ΣR)*[(pHi−pHx)*(Rb2+2Rs)+Rb1*(pHi−10)];
3) Eglass=(S/ΣR)*[(pHi−pHx)*(Rb2+2Rs)+Rb1*(10−pHx)]; and
4) Eglass=(S/IR)*[(pHi−pHx)*(Rb2+2Rs)].

Case 1 (no coating) is the equation for an uncoated electrode system, as expected.

Case 2 (external coating) shows a system where the slope is reduced by the factor K, with an added offset included. The factor K is defined as:

$$K = (Rb2+2Rs)/\Sigma R \quad (3)$$

And an offset term is added.

Case 3 (internal coating) shows a system where the slope is not reduced, but an offset term is added.

Case 4 shows a system like that of Case 1 where no offset term appears, and the slope is reduced by the factor K.

The values for Rs, the resistance through the hydrated layer of glass, are assumed to be very much less than those for the un-hydrated bulk glass sections. Rb1 and Rb2 can be related to the percent of the glass area covered. Assuming a constant bulb thickness, the volume resistivity of the glass gives a conductance per unit area.

Let $\sigma_t$ be the total conductance of the bulb area, Ac be the percent of the area covered by a coating which is assumed to be an electrical insulator, and Anc be the percent of the area not covered by the coating. Note that the areas Ac and Anc add up to one hundred percent of the area of the pH-sensitive glass 122. Here, the Rb2 term (the resistance of coated area) and the Rb1 term (the resistance of the un-coated area) are given as:

$$Rb2 = 1/[\sigma_t * Anc] \quad (4)$$

$$Rb1 = 1/[\sigma_t * Ac] \quad (5)$$

The reduced slope S' is then given by:

$$S' = S*Rb2/(Rb1+Rb2) \quad (6)$$

$$S' = S*\{1/[\sigma_t*Anc]\}/\{1/[\sigma_t*Anc]+1/[\sigma_t*Ac]\} \quad (7)$$

Which simplifies to:

$$S' = S*Anc/100 = S*(1-Ac/100) \quad (8)$$

The result is the ability to control the voltaic response per unit change in pH measurement value. This model is a simple representation of a complex structure, but does gives results that are surprisingly close to experimental findings.

Figure 4:
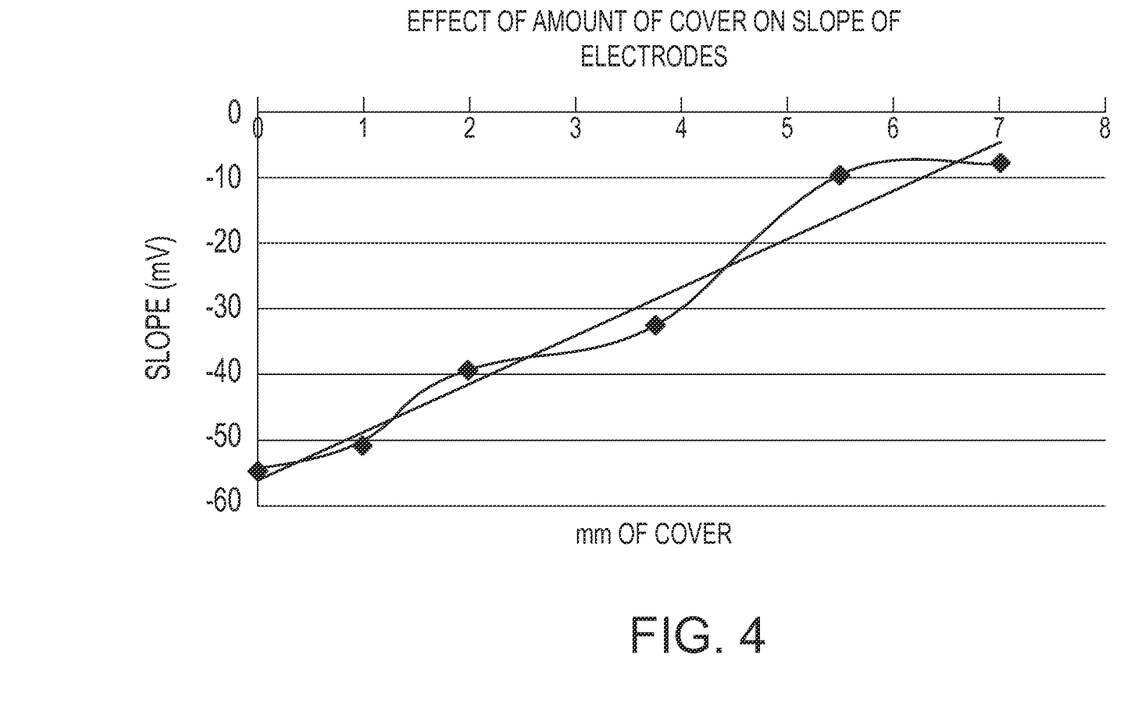
FIG. 4 is a graph of pH slope versus area of a pH-sensitive glass that is covered with a mask.

FIG. 4 is a graph of pH slope versus area of the pH-sensitive glass 122 that is covered with the mask 124. The graph shows that empirical measurements confirm the math shown and discussed above. It can be seen from the graph that the response slope varies substantially linearly with masked area percentage. It should be understood that the slope S of the electrode voltaic response can be varied according to the invention. The graph shows that a desired voltaic response slope can be achieved.

It should be understood that, unlike specially manufactured low-slope pH-sensitive glass, the slope S of the electrode response of the low-slope pH electrode 100 can be of any desired value. The slope S for the low-slope pH electrode 100 can be changed after manufacture. The slope S for the low-slope pH electrode 100 can be modified, reconfigured, or recalibrated. The slope S for the low-slope pH electrode 100 can be changed at any time, including removing all or part of the mask 124 or by adding an overlying or additional mask 124, including adding mask material that adds to and/or overlaps an existing mask 124.

Figure 5:
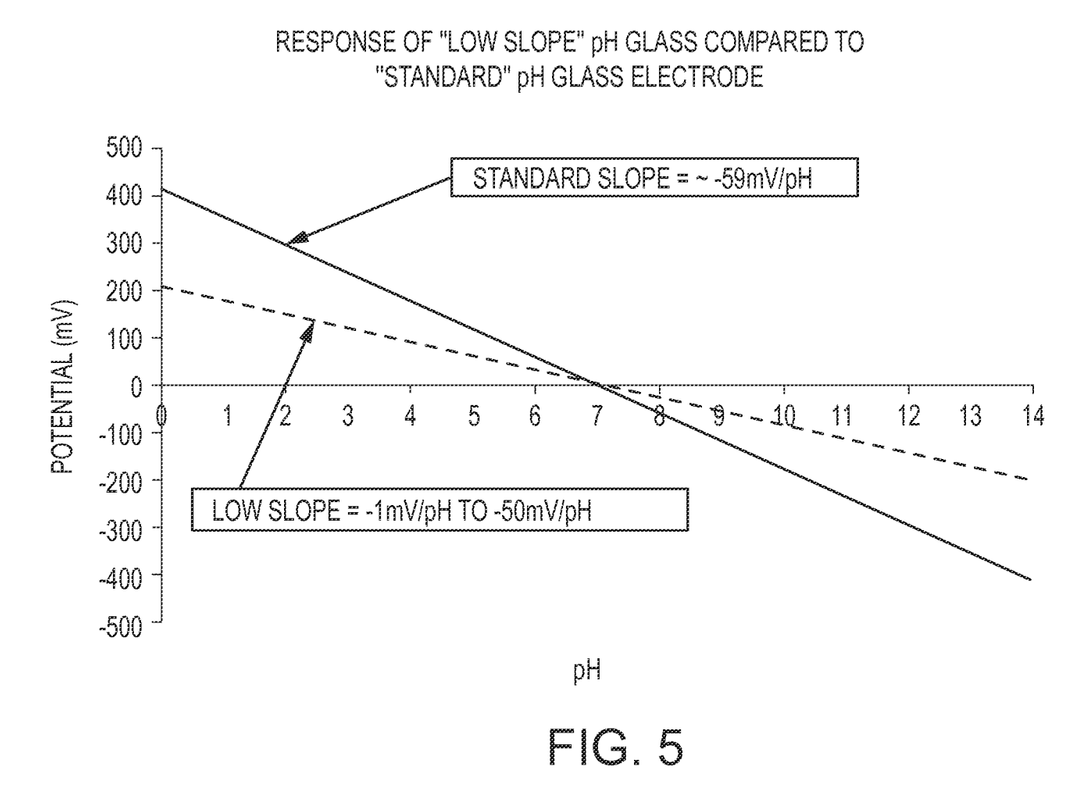
FIG. 5 is a graph showing an example of a low-slope pH electrode according to any embodiment of the invention as compared to a standard (i.e., prior art) pH electrode.

FIG. 5 is a graph showing an example of a low-slope pH electrode 100 according to any embodiment of the invention as compared to a standard (i.e., prior art) pH electrode, when both voltaic responses are plotted in a conventional manner. The low-slope pH electrode 100 according to the invention has a reduced pH sensitivity. Therefore, when plotted in a chart, the response line of the low-slope pH electrode 100 is less steep in slope, such as having a slope of between −1 mV/pH unit and −50 mV/pH unit, for example. The figure also shows the voltaic response of a standard pH electrode 100 for S=−59 mV/pH (this slope chosen merely for example). A wide variety of glass formulations will respond to pH in such a way to produce a standard slope of approximately −59 mV/pH unit. Essentially all established formulations for pH glass produce this standard slope of approximately −59 mV/pH unit.

Figure 6:
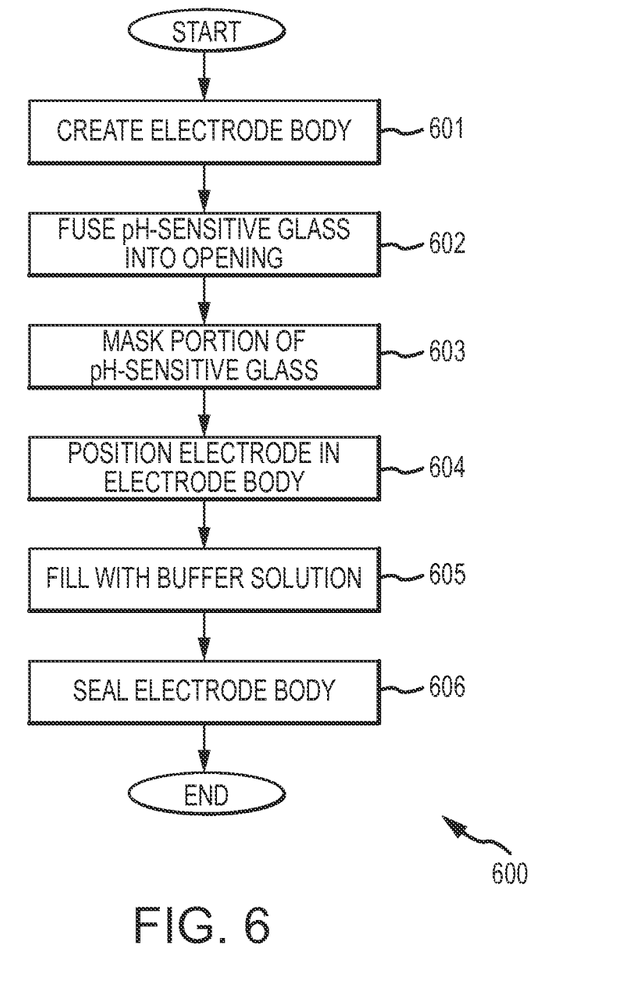
FIG. 6 is a flowchart of a method of forming a low-slope pH electrode according to an embodiment of the invention.

FIG. 6 is a flowchart of a method of forming a low-slope pH electrode according to an embodiment of the invention. In step 601, an electrode body is created. The electrode body is substantially hollow and may include at least two openings in the electrode body wall; a sensor opening for receiving the pH-sensitive glass and an opening or open end for inserting components. The electrode body can be of any desired shape, size, internal volume, durability, composition, wall thickness, et cetera. In some embodiments, the electrode body is made of standard glass that does not react to a pH of solutions inside and outside of the electrode. The electrode body can include the sensor opening designed to receive a piece of pH-sensitive material, such as pH-sensitive glass, for example.

In step 602, a piece of pH-sensitive glass is installed into the sensor opening, such as by fusing a piece of pH-sensitive glass to the surrounding glass of the electrode body.

In step 603, a portion of the pH-sensitive glass is masked. The mask covers a predetermined portion of the pH-sensitive glass. The mask therefore lowers/decreases the slope of an ionic exchange performed by the pH-sensitive glass.

In step 604, an appropriate electrode element is positioned in the electrode body.

In step 605, the electrode body is substantially filled with a pH buffer solution.

In step 606, the electrode body is substantially sealed, such as by a plug or seal. The completed low-slope pH electrode is substantially sealed to prohibit fluid transfer into, or out of, the electrode body.

The mask can comprise material added after the electrode body has been formed. The mask therefore can be later added, if desired.

The mask can be temporary or short-term, if desired. The mask may be removable. The mask may be repositionable. The mask may be re-usable.

The mask may be customizable and may be sized for a particular electrode application.

The mask maybe formed to size before application. Alternatively, the mask may be applied to the electrode body and then cut, trimmed, abraded, or removed in some manner, such as by laser trimming.

The mask may be formed of glass. The mask may be formed of materials other than glass, such as plastic, for example. The mask may be substantially rigid or substantially flexible. The mask may be fused with or become part of the electrode body. The mask may be separate from and removably or permanently affixed to the electrode body.

The mask may not require any fusing or glazing. The mask may not require high temperatures for application or any of the expensive equipment needed for generating high temperatures over long time periods for fusing or glazing. The mask may be applied at temperatures below a glass transition point or glass melting point.

The mask 124 in some embodiments is independent of the electrode body 102. Alternatively, the mask 124 may be bonded, fused, or otherwise joined to one or both of the bulk glass 102 or the pH-sensitive glass 122. In these embodiments, the mask 124 may become a part of the electrode structure.

In some embodiments, the mask 124 may be affixed to the pH-sensitive glass 122 around only a perimeter, creating a volume between the mask 124 and the pH-sensitive glass 122. Consequently, a buffer fluid, air, or other non-conducting gas can fill the volume.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention. Accordingly, the scope of the invention should be determined from the following claims.

What is claimed is:

1. A low-slope pH electrode, comprising:
    an electrode body;
    a pH sensitive glass fused into the electrode body, with the pH-sensitive glass including a predetermined area;
    a mask formed over a predetermined portion of the predetermined area of the pH sensitive glass in order to form a low-slope pH characteristic, wherein at least a portion of an ion exchange performed by the pH-sensitive glass is blocked by the mask;
    an electrode element positioned inside the electrode body;
    a pH buffer solution substantially filling the electrode body; and
    a seal that substantially seals the electrode body.

2. The low-slope pH electrode of claim 1, with the mask comprising a non-hydrogen ion responsive material.

3. The low-slope pH electrode of claim 1, with the mask comprising a non-hydronium ion responsive material.

4. The low-slope pH electrode of claim 1, with the mask comprising a substantially non-porous material.

5. The low-slope pH electrode of claim 1, with the mask comprising a minimally porous material.

6. The low-slope pH electrode of claim 1, with the mask formed on an external surface of the pH-sensitive glass.

7. The low-slope pH electrode of claim 1, wherein the mask is formed of a predetermined thickness.

8. The low-slope pH electrode of claim 1, wherein the mask is a predetermined pattern.

9. The low-slope pH electrode of claim 1, with the mask formed on both an external surface or an internal surface of the pH-sensitive glass.

10. The low-slope pH electrode of claim 1, wherein the low-slope pH electrode forms a non-Nernstian pH electrode.

11. A method of forming a low-slope pH electrode, comprising:
    forming an electrode body including a sensor opening;
    fusing a pH-sensitive glass of a predetermined area into the sensor opening; and
    masking a predetermined portion of the predetermined area in order to form a low-slope pH characteristic, wherein at least a portion of an ion exchange performed by the pH-sensitive glass is blocked.

12. The method of claim 11, further comprising:
    positioning an electrode element inside the electrode body;
    substantially filing the electrode body with a pH buffer solution; and
    substantially sealing the electrode body.

13. The method of claim 11, with the mask comprising a non-hydrogen ion responsive material.

14. The method of claim 11, with the mask comprising a non-hydronium ion responsive material.

15. The method of claim 11, with the mask comprising a substantially non-porous material.

16. The method of claim 11, with the mask comprising a minimally porous material.

17. The method of claim 11, wherein the mask is formed on an external surface of the pH-sensitive glass.

18. The method of claim 11, wherein the mask is formed of a predetermined thickness.

19. The method of claim 11, wherein the mask is formed in a predetermined pattern.

20. The method of claim 11, wherein the mask is formed on one or both of an external surface or an internal surface of the pH-sensitive glass.

21. The method of claim 11, with the low-slope pH electrode comprising a non-Nernstian pH electrode.

* * * * *